United States Patent
Ikami

(10) Patent No.: US 7,794,661 B2
(45) Date of Patent: Sep. 14, 2010

(54) METHOD AND SYSTEM FOR DETECTING FLUORESCENCE FROM MICROARRAY DISK

(75) Inventor: Seishi Ikami, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 927 days.

(21) Appl. No.: 11/492,911

(22) Filed: Jul. 26, 2006

(65) Prior Publication Data

US 2007/0026532 A1 Feb. 1, 2007

(30) Foreign Application Priority Data

Jul. 26, 2005 (JP) .............................. 2005-215448

(51) Int. Cl.
*G01N 21/64* (2006.01)
*C12M 3/00* (2006.01)
*G01N 21/76* (2006.01)
*G01N 33/53* (2006.01)
*C12M 1/34* (2006.01)

(52) U.S. Cl. ..................... 422/82.08; 422/82.07; 435/6; 435/7.1; 435/287.1; 435/287.2; 436/172

(58) Field of Classification Search ........................ None
See application file for complete search history.

(56) References Cited

U.S. PATENT DOCUMENTS

| | | | |
|---|---|---|---|
| 4,778,763 A | 10/1988 | Makiguchi et al. | |
| 6,504,167 B2 | 1/2003 | Ikami | |
| 6,563,584 B1 | 5/2003 | Yurino et al. | |
| 6,963,397 B2 | 11/2005 | Suzuki et al. | |
| 2001/0046712 A1* | 11/2001 | Hang et al. | ............... 436/172 |
| 2003/0059803 A1* | 3/2003 | Werner et al. | ................ 435/6 |
| 2005/0048595 A1 | 3/2005 | Yamatsu et al. | |

FOREIGN PATENT DOCUMENTS

| | | |
|---|---|---|
| JP | 61241639 A | 10/1986 |
| JP | 2000304698 A | 11/2000 |
| JP | 2000321206 A | 11/2000 |
| JP | 2004-333333 A | 11/2004 |

OTHER PUBLICATIONS

Japanese Office Action corresponding to Japanese Patent Application No. 2005-215448 dated Mar. 2, 2010.

* cited by examiner

*Primary Examiner*—Jill Warden
*Assistant Examiner*—Neil Turk
(74) *Attorney, Agent, or Firm*—Sughrue Mion, PLLC

(57) ABSTRACT

In a fluorescence detection method: each of one or more biological specimens is irradiated with excitation light while a substrate disk is rotated, where the one or more biological specimens are labeled with a fluorescent material and fixed on the substrate disk. Fluorescence which is emitted from each of the one or more biological specimens is detected when a predetermined time elapses since the biological specimen is irradiated with the excitation light.

5 Claims, 2 Drawing Sheets

METHOD AND SYSTEM FOR DETECTING FLUORESCENCE FROM MICROARRAY DISK

BACKGROUND OF THE INVENTION

1. Field of the Invention

The present invention relates to a fluorescence detection method and a fluorescence detection system in which a fluorescence-labeled biological specimen is irradiated with excitation light, and fluorescence emitted from the biological specimen by the irradiation is detected.

2. Description of the Related Art

Conventionally, the fluorescence detection systems which use fluorescent material as a labeling material are known in the field of biochemistry. It is possible to investigate gene arrangement or gene expression levels, isolate or identify protein, or evaluate molecular weight or characteristics of protein, by reading fluorescent images obtained by use of a fluorescence detection system.

For example, a fluorescent dye is added to a solution containing DNA fragments which are to be electrophoresed, and thereafter the DNA fragments are electrophoresed on a gel support. Alternatively, DNA fragments are electrophoresed on a gel support which contains a fluorescent dye. After the electrophoresis, the electrophoresed DNA fragments are labeled, for example, by soaking the gel support in a solution containing a fluorescent dye. Then, the DNA distribution on the gel support can be detected by exciting the fluorescent dye with excitation light, detecting fluorescence emitted from the excited fluorescent dye, and producing an image of the detected fluorescence.

Alternatively, it is possible to detect a DNA distribution by using the Southern blotting technique as follows.

(a) DNA fragments are electrophoresed on a gel support.
(b) DNA fragments are denaturated.
(c) At least a portion of the DNA fragments is transcribed onto another support for transcription, which is made of, for example, nitrocellulose, in accordance with the Southern blotting technique.
(d) The denaturated DNA fragments are hybridized with a probe which is prepared by labeling a DNA or RNA complementary to an objective DNA with a fluorescent dye, so that only DNA fragments which are complementary to the probe DNA or probe RNA are selectively labeled.
(e) The fluorescent dye is excited with excitation light, fluorescence emitted from the fluorescent dye is detected, and an image of the detected fluorescence is produced, so that the distribution of the objective DNA on the support for transcription is detected.

In recent years, the microarray analysis system as a biochemical analysis system has been receiving attention. For example, in the microarray analysis system in which a fluorescent material is used as a labeling material, a number of separate spots of specifically binding materials are formed on different positions on a support such as a slide glass or membrane filter by putting drops of the specifically binding materials on the support by use of a spotter device, where each of the specifically binding materials can be specifically bound to a substance of biological origin such as a hormone, tumor marker, enzyme, immune body, antigen, abzyme, other protein, or nucleic acid (e.g., cDNA, DNA, RNA), and the nucleotide sequences, and the nucleotide lengths, compositions, and the like of the specifically binding materials are known. Subsequently, a substance of biological origin labeled with a fluorescent labeling material such as a (fluorescent) dye is specifically bound to (hybridized with) the spots of the specifically binding materials on the support, where the substance of biological origin is obtained in advance from an organism by extraction, isolation, and the like, and may be chemically processed or chemically modified. Thereafter, analysis of the substance of biological origin is performed by irradiating the above microarray with excitation light, and photoelectrically detecting fluorescence or the like emitted from the labeling material.

In the conventional microarray analysis systems, devices which produce a two-dimensional image of fluorescence emitted from the spots (which are two-dimensionally arrayed in a grid pattern) for reading are mainly used. For example, U.S. Pat. No. 6,504,167 discloses a device which reads a two-dimensional distribution of fluorescence by use of a line scanning system, and produces an image of the two-dimensional distribution of fluorescence. However, in the line scanning system, it is necessary to repetitively move an excitation-light irradiation unit and a fluorescence reception unit, so that the inertia management in the mechanical units is required, and it is difficult to downsize the above device.

On the other hand, for example, Japanese Unexamined Patent Publication No. 2004-333333 and U.S. Patent Application Publication No. 20050048595 disclose other systems for reading fluorescence emitted from the spots on a substrate disk. In the disclosed systems, spots of the hybridized specifically binding materials are concentrically or spirally arrayed on the substrate disk, and reference marks enabling determination of the positions of the spots are arranged on the substrate disk. Then, information on the fluorescence is read from the spots by one-dimensionally (concentrically or spirally) scanning the spots on the substrate disk.

Specifically, U.S. Patent Application Publication No. 20050048595 discloses a method for analyzing the strength of bonding between a target substance and materials for detection. In the disclosed method, drops of solutions containing the materials for detection are put on predetermined positions on the substrate disk while rotating the substrate disk, and the drops of solutions containing the materials for detection are solidified on the substrate disk. Then, drops of a solution containing the target substance labeled with a fluorescent labeling material are put on the solidified materials for detection so as to cause reaction between the target substance and the materials for detection, and portions of the target substance which are not used in the reaction are washed off. Thereafter, portions of the target substance which have reacted with the materials for detection are irradiated with excitation light while the substrate disk is rotated, fluorescence emitted from the fluorescent label is detected with a detector, and the detected intensity of the fluorescence is analyzed for obtaining the strength of bonding between the target substance and the materials for detection.

In the systems for fluorescence detection by use of the substrate disk which are disclosed in Japanese Unexamined Patent Publication No. 2004-333333 and U.S. Patent Application Publication No. 20050048595, the fluorescence is detected at the same time as the irradiation of the excitation light, the lens which makes the excitation light converge on predetermined spots also collect the fluorescence emitted from the spots, and the optical axis of the excitation light is identical to the optical axis of the fluorescence emitted from the spots. However, when the excitation light enters the fluorescence detector, the excitation light produces noise, and lowers the signal-to-noise ratio in the signal indicating the detected fluorescence. Therefore, an optical filter for cutting off the excitation light is arranged in front of the light reception surface of the fluorescence detector in order to prevent entrance of the excitation light into the fluorescence detector.

Nevertheless, the above optical filter cannot completely prevent entrance of the excitation light into the fluorescence detector. Therefore, conventionally, it is difficult to achieve sufficient signal-to-noise ratio in the signal indicating the detected fluorescence.

SUMMARY OF THE INVENTION

The present invention has been developed in view of the above circumstances.

The first object of the present invention is to provide a fluorescence detection method which detects fluorescence emitted from specimens on a substrate disk (microarray disk), and can achieve a high signal-to-noise ratio in the signal indicating the detected fluorescence.

The second object of the present invention is to provide a fluorescence detection system which detects fluorescence emitted from specimens on a substrate disk (microarray disk), and can achieve a high signal-to-noise ratio in the signal indicating the detected fluorescence.

In order to accomplish the first object, according to the first aspect of the present invention, there is provided a fluorescence detection method comprising the steps of: (a) performing irradiation of each of one or more biological specimens with excitation light while rotating a substrate disk, where the one or more biological specimens are labeled with a fluorescent material and fixed on the substrate disk; and (b) detecting fluorescence which is emitted from each of the one or more biological specimens when a predetermined time elapses since the biological specimen is irradiated with the excitation light.

In order to accomplish the second object, according to the second aspect of the present invention, there is provided a fluorescence detection system comprising: a substrate disk being rotatable and having a specimen-holding area on which a one or more fluorescence-labeled biological specimens are fixed; a rotation unit which rotates the substrate disk; an excitation-light irradiation unit which performs irradiation of each of the one or more biological specimens with excitation light; a fluorescence-detection unit which detects fluorescence emitted from each of the one or more biological specimens; and a control unit which controls the rotation unit, the excitation-light irradiation unit, and the fluorescence-detection unit so that each of the one or more biological specimens is irradiated with the excitation light while the substrate disk is rotated by the rotation unit, and the fluorescence-detection unit detects fluorescence emitted from each of the one or more biological specimens when a predetermined time elapses since the biological specimen is irradiated with the excitation light.

In the fluorescence detection method according to the first aspect of the present invention and the fluorescence detection system according to the second aspect of the present invention, the irradiation with the excitation light is performed while the substrate disk is rotated, and the fluorescence emitted from each of the one or more biological specimens is detected when a predetermined time elapses since the biological specimen is irradiated. That is, delayed fluorescence is detected. Since the fluorescence is detected after irradiation with the excitation light is completed, the excitation light does not enter the fluorescence-detection unit. Therefore, the fluorescence-detection unit is free from the noise produced by the excitation light, and can output a detection signal with high signal-to-noise ratio.

Preferably, the above fluorescence detection system according to the second aspect of the present invention may further comprise the following additional features (i) to (v).

(i) The substrate disk, the excitation-light irradiation unit, and the fluorescence-detection unit may be arranged so that the excitation-light irradiation unit applies the excitation light to a first position on the substrate disk for irradiating each of the one or more biological specimens, the fluorescence-detection unit detects fluorescence received from a second position on the substrate disk for detecting fluorescence emitted from the biological specimen, and the first position and the second position are at identical radial distances from the center of rotation of the substrate disk and at angular positions which are different by a predetermined angle.

(ii) The one or more biological specimens may be labeled with a fluorescent material having a fluorescent lifetime on the order of microseconds to milliseconds. An example of the fluorescent material having a fluorescent lifetime on the order of microseconds is Sypro Ruby, available from Molecular Probe Inc., where Sypro is a registered trademark of Molecular Probe Inc. In addition, an example of the fluorescent material having a fluorescent lifetime on the order of milliseconds is DELFIA, available from PerkinElmer Life Science Inc., where DELFIA is a registered trademark of PerkinElmer Life Science Inc.

(iii) The specimen-holding area may be realized by one or more grooves spirally or concentrically arranged on the substrate disk. In this case, it is possible to prevent irradiation of a spot adjacent to an objective spot when the one or more biological specimens are fixed in a plurality of spots on the substrate disk.

(iv) In the fluorescence detection system having the additional feature (iii), each of the one or more grooves may have a width which is greater than a diameter of a light spot which the excitation light forms on the substrate disk.

(v) The substrate disk may be opaque to the excitation light. In this case, it is possible to prevent propagation of the excitation light through the substrate disk, and undesirable excitation of biological specimens in the vicinity of the objective spot to which the excitation light is applied.

DESCRIPTION OF PREFERRED EMBODIMENTS

Figure 1:
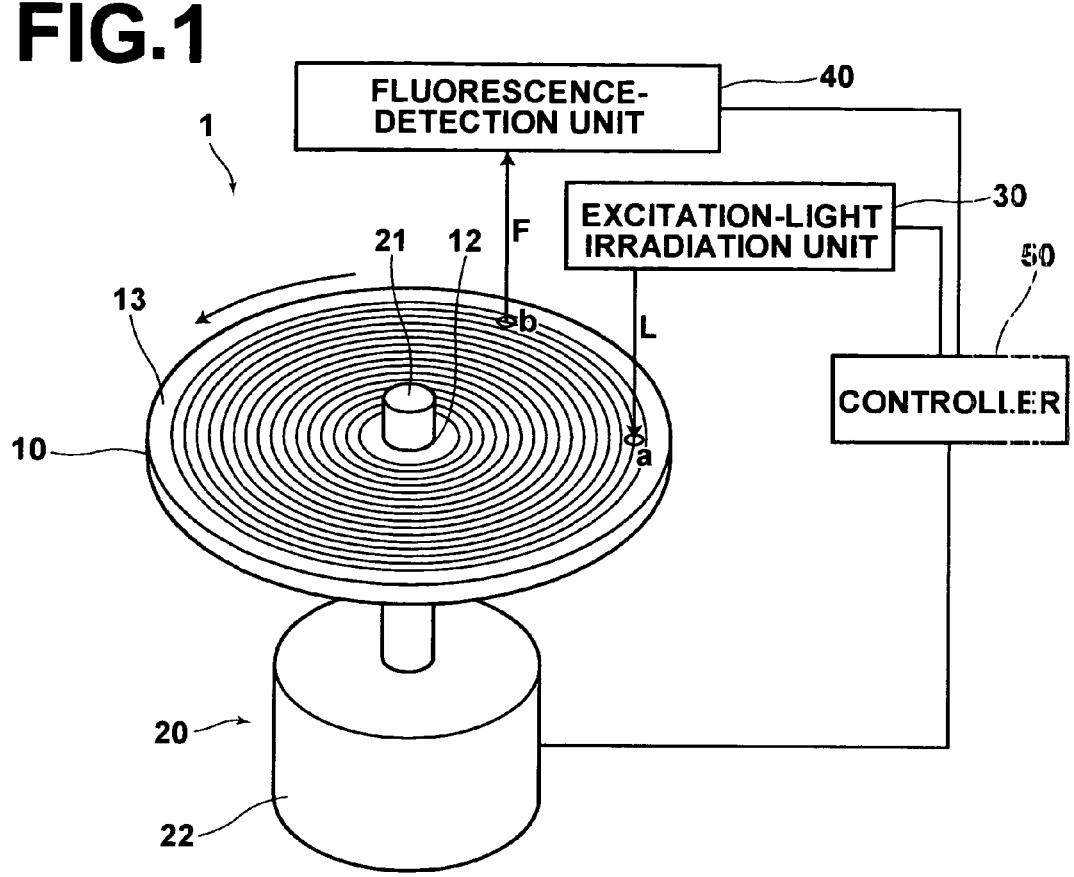
FIG. 1 is a diagram schematically illustrating a fluorescence detection system according to a first embodiment of the present invention, where a microarray disk is used.

Preferred embodiments of the present invention are explained in detail below with reference to drawings. In the drawings, equivalent elements and constituents are indicated by the same reference numbers even in drawings for different embodiments, and descriptions of the equivalent elements or constituents are not repeated in the following explanations unless necessary.

First Embodiment

FIG. 1 is a diagram schematically illustrating a fluorescence detection system according to the first embodiment of the present invention.

As illustrated in FIG. 1, the fluorescence detection system 1 according to the first embodiment comprises a microarray disk 10, a rotation unit 20, an excitation-light irradiation unit 30, a fluorescence-detection unit 40, and a controller 50.

The microarray disk 10 is constituted by a rotatable substrate disk, where a surface of the microarray disk 10 includes a specimen-holding area, and fluorescence-labeled biological specimens are fixed on the specimen-holding area. The rotation unit 20 rotates the microarray disk 10. The excitation-light irradiation unit 30 irradiates each of the biological specimens (fixed on the microarray disk 10) with excitation light L. The fluorescence-detection unit 40 detects fluorescence F emitted from each of the biological specimens. The controller 50 controls the rotation unit 20, the excitation-light irradiation unit 30, and the fluorescence-detection unit 40.

Figure 2A:
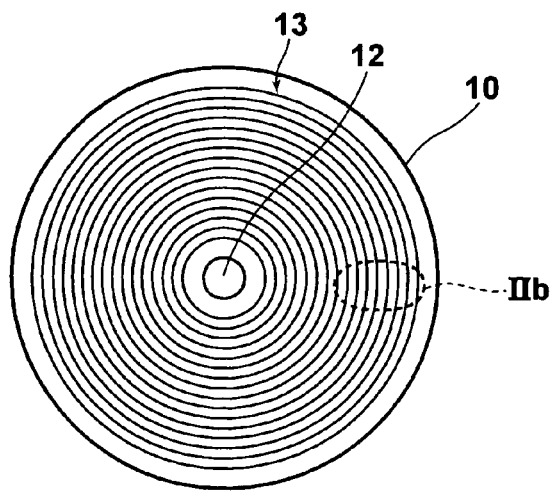
FIG. 2A is a top view the microarray disk.
Figure 2B:
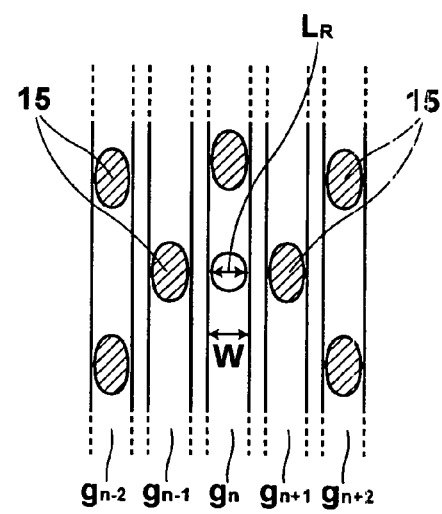
FIG. 2B is a magnified view of a portion of the microarray disk of FIG. 2A.

FIG. 2A is a top view the microarray disk 10, and FIG. 2B is a magnified view of a portion of the microarray disk 10. The substrate disk constituting the microarray disk 10 is formed of a material which is opaque to the excitation light L, and has a central hole 12 at the center of the microarray disk 10. A plurality of grooves . . . , $g_{n-2}$, $g_{n-1}$, $g_n$, $g_{n+1}$, $g_{n+2}$, . . . are concentrically formed on a surface 13 of the substrate disk, and the biological specimens 15 are fixed in a plurality of spots in the grooves . . . , $g_{n-2}$, $g_{n-1}$, $g_n$, $g_{n+1}$, $g_{n+2}$, . . . , where the biological specimens 15 are fluorescence labeled. The width W of each of the grooves . . . , $g_{n-2}$, $g_{n-1}$, $g_n$, $g_{n+1}$, $g_{n+2}$, . . . is greater than the diameter $L_R$ of the light spot formed on the surface 13 of the microarray disk 10 by the excitation light L. In other words, the excitation light L is focused to the light spot having the diameter $L_R$ smaller than the width W of each of the grooves . . . , $g_{n-2}$, $g_{n-1}$, $g_n$, $g_{n+1}$, $g_{n+2}$ . . . . For example, each of the grooves . . . , $g_{n-2}$, $g_{n-1}$, $g_n$, $g_{n+1}$, $g_{n+2}$, . . . has the depth of 60 micrometers and the width of 100 micrometers. The spots of the fluorescence-labeled biological specimens 15 are arranged along the centers of the grooves . . . , $g_{n-2}$, $g_{n-1}$, $g_n$, $g_{n+1}$, $g_{n+2}$, . . . at intervals of 300 micrometers. For example, the excitation light L is a Gaussian beam with a diameter of 30 micrometers, which is smaller than the width W (100 micrometers) of each of the grooves . . . , $g_{n-2}$, $g_{n-1}$, $g_n$, $g_{n+1}$, $g_{n+2}$ . . . .

Since the grooves . . . , $g_{n-2}$, $g_{n-1}$, $g_n$, $g_{n+1}$, $g_{n+2}$, . . . for holding the spots of the biological specimens 15 are arranged on the surface 13 of the substrate disk, and only the inside of the grooves . . . , $g_{n-2}$, $g_{n-1}$, $g_n$, $g_{n+1}$, $g_{n+2}$, . . . is irradiated with the excitation light L, it is possible to excite only the biological specimen in an objective spot without undesirable irradiation of biological specimens in other spots adjacent to the objective spot. Therefore, it is possible to prevent collection of fluorescence emitted from the biological specimens in the adjacent spots, and production of noise by the collection of such fluorescence.

In addition, the microarray disk 10 has a single-layer structure in which the grooves . . . , $g_{n-2}$, $g_{n-1}$, $g_n$, $g_{n+1}$, $g_{n+2}$, . . . are formed on the surface 13, and the substrate disk constituting the microarray disk 10 may be a plate of acrylic resin in which carbon particles are dispersed, or a plate of aluminum which is black-alumite processed after the formation of the grooves . . . , $g_{n-2}$, $g_{n-1}$, $g_n$, $g_{n+1}$, $g_{+2}$ . . . .

Further, after the biological specimens 15 are fluorescence-labeled, the specimen-fixed side of the microarray disk 10, on which the spots of biological specimens 15 are arranged, may be processed for preventing scattering and contamination of the labeled substances. For example, the specimen-fixed side of the microarray disk 10 may be coated with a methacrylic resin which is transparent to the excitation light L and the fluorescence F and has a uniform thickness.

Since the substrate disk constituting the microarray disk 10 is opaque to the excitation light L, it is possible to prevent propagation of the excitation light L through the substrate disk, and undesirable excitation of the biological specimens in the vicinity of the objective spot to which the excitation light is applied.

It is preferable that the biological specimens 15 are labeled with a fluorescent material having a fluorescent lifetime on the order of microseconds to milliseconds.

The rotation unit 20 comprises a spindle 21, a spindle motor 22, and a rotary encoder (not shown). The spindle 21 is inserted through the central hole 12 of the microarray disk 10 for holding the microarray disk 10.

As illustrated in FIG. 1, the excitation-light irradiation unit 30 and the fluorescence-detection unit 40 are arranged above the specimen-fixed side of the microarray disk 10 so that the excitation-light irradiation unit 30 applies the excitation light L to a first position a on the microarray disk 10 for irradiating the biological specimen in each of the plurality of spots, the fluorescence-detection unit 40 detects fluorescence received from a second position b on the microarray disk 10 for detecting fluorescence emitted from the biological specimen in the spot, and the first position a and the second position b are at identical radial distances from the center of rotation of the microarray disk 10 and at angular positions which are different by a predetermined angle.

In addition, the excitation-light irradiation unit 30 and the fluorescence-detection unit 40 can be moved in the radial directions by a movement mechanism (not shown) so that the first position a and the second position b are in an identical one of the grooves . . . , $g_{n-2}$, $g_{n-1}$, $g_n$, $g_{n+1}$, $g_{n+2}$, . . . all the times during the measurement.

Figure 3:
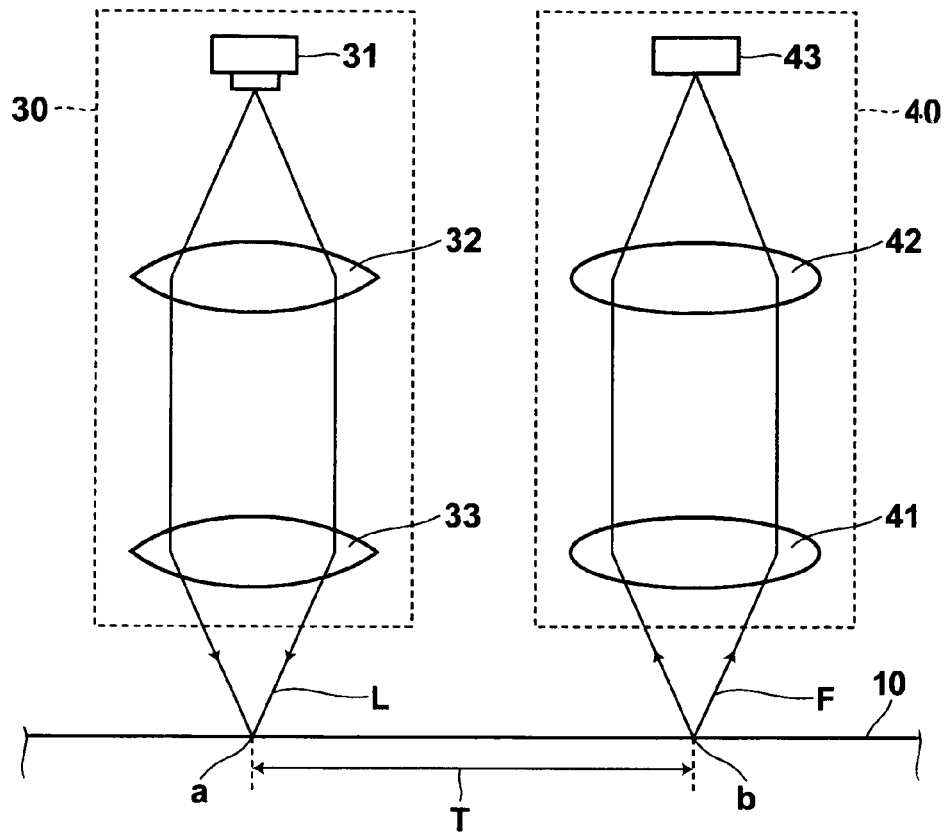
FIG. 3 is a diagram schematically illustrating an excitation-light irradiation unit and a fluorescence-detection unit.

FIG. 3 is a diagram schematically illustrating the excitation-light irradiation unit 30 and the fluorescence-detection unit 40.

As illustrated in FIG. 3, the excitation-light irradiation unit 30 comprises a laser diode 31, a collimator lens 32, and a condensing lens 33. The excitation-light irradiation unit 30 emits the excitation light L, the collimator lens 32 collimates the excitation light L emitted from the laser diode 31, and the condensing lens 33 makes the collimated excitation light L converge on the biological specimen in each spot on the microarray disk 10.

In addition, the fluorescence-detection unit 40 comprises a condensing lens 41, a lens 42, and an optical detector 43. The condensing lens 41 collects the fluorescence F emitted from the biological specimen in each spot on the microarray disk 10, the lens 42 makes the fluorescence F converge at the optical detector 43, and the optical detector 43 detects the fluorescence F. For example, the optical detector 43 is a photodiode, a photomultiplier (phototube), or an avalanche photodiode.

The controller 50 controls the rotation unit 20, the excitation-light irradiation unit 30, and the fluorescence-detection unit 40 so that the excitation-light irradiation unit 30 irradiates each of the biological specimens with the excitation light L while the rotation unit 20 rotates the microarray disk 10, and the fluorescence-detection unit 40 detects the fluorescence F emitted from the biological specimen when a predetermined time elapses since the biological specimen is irradiated. Specifically, the controller 50 changes the rotation speed of the micro array disk 10 according to the fluorescent lifetime of the fluorescent material as the fluorescent label, the distance between the first and second positions a and b along the corresponding groove, and the like, makes the excitation-light irradiation unit 30 and the fluorescence-detection unit 40 perform the irradiation with the excitation light L and the detection of the fluorescence F on the basis of position information obtained by the rotary encoder, and performs other control operations.

Although the concentric grooves ..., $g_{n-2}$, $g_{n-1}$, $g_n$, $g_{n+1}$, $g_{n+2}$, ... are arranged on the microarray disk 10 illustrated in FIG. 1, alternatively, it is possible to spirally arrange one or more grooves on the substrate disk. In this case, the controller 50 also controls the excitation-light irradiation unit 30 and the fluorescence-detection unit 40 so that the first position a to which the excitation-light irradiation unit 30 applies the excitation light L for irradiating the biological specimen in each of the plurality of spots and the second position b from which the fluorescence-detection unit 40 receives fluorescence for detecting fluorescence emitted from the biological specimen in the spot are at identical radial distances from the center of rotation of the microarray disk 10.

Fluorescence Detection Method

Hereinbelow, the fluorescence detection method used in the fluorescence detection system 1 according to the first embodiment is explained.

The excitation light L is emitted from the laser diode 31, collimated by the collimator lens 32, condensed by the condensing lens 33, and applied to the biological specimen in each spot on the microarray disk 10. At this time, the excitation light L is focused by the condensing lens 33 so that the light spot formed on the microarray disk 10 by the excitation light L has a diameter $L_R$ smaller than the width W of each groove.

When a fluorescence-labeled biological specimen in a spot at the first position a is irradiated with the excitation light L, the biological specimen emits fluorescence F. Since the microarray disk 10 is rotated, the irradiated biological specimen in the spot moves to the second position b when the predetermined time elapses since the irradiation of the biological specimen in the spot, so that fluorescence F emitted from the biological specimen can be received and detected from the second position b when the predetermined time elapses since the irradiation of the biological specimen in the spot. The fluorescence F emitted from the biological specimen is collected and collimated by the condensing lens 41 (which is arranged above the specimen-fixed side of the microarray disk 10), and led to the optical detector 43 through the lens 42. Since the time T which elapses since the irradiation of the biological specimen at the first position a until the emission of the fluorescence F from the biological specimen at the second position b is determined by the rotation speed of the microarray disk 10, the controller 50 controls the excitation-light irradiation unit 30 and the fluorescence-detection unit 40 so that the fluorescence-detection unit 40 receives fluorescence emitted from the irradiated biological specimen when the time T elapses since the excitation-light irradiation unit 30 irradiates the biological specimen with the excitation light L.

As explained above, the fluorescence is detected when the time T elapses since the excitation-light irradiation unit 30 irradiates the biological specimen with the excitation light L. Therefore, when the fluorescence-detection unit 40 detects the fluorescence, the excitation light L does not enter the fluorescence-detection unit 40, so that no noise is produced by the excitation light L in the fluorescence-detection unit 40, and the fluorescence-detection unit 40 can output a detection signal with high signal-to-noise ratio.

Next, details of an example of the fluorescence detection method used in the fluorescence detection system 1 according to the first embodiment are as follows.

The labeling material used in the first embodiment is DELFIA, which is available from PerkinElmer Life Science Inc., and has a fluorescent lifetime of several microseconds. The fluorescence is detected after a delay of one millisecond after the irradiation with the excitation light L. For example, the microarray disk 10 has the diameter of 12 cm, which is identical to the widely used compact disk (CD).

The excitation-light irradiation unit 30 and the fluorescence-detection unit 40 are arranged so that the first and second positions a and b are at identical radial distances from the center of rotation of the microarray disk 10 and at different angular positions, which are different by the angle q. The angle q is determined at the rotation speed of the microarray disk 10. For example, the angle q is 45 degrees when the rotation speed of the microarray disk 10 is 7,500 rpm, 90 degrees when the rotation speed of the microarray disk 10 is 15,000 rpm, and 180 degrees when the rotation speed of the microarray disk 10 is 30,000 rpm. In particular, when the angle q is 180 degrees, the spindle 21 is located between the first and second positions a and b, so that the fluorescence-detection unit 40 is shaded by the spindle 21 from the excitation light L. Therefore, in order to prevent entrance of the excitation light L into the fluorescence-detection unit 40 by propagation through the surface of the microarray disk 10, It is preferable that the angle q is 180 degrees.

The excitation light L may be emitted from the laser diode 31 by either of continuous-wave oscillation and pulsed oscillation. However, it is preferable to use a triggered pulsed laser in order to suppress deterioration of the fluorescent material (dye).

Indexes for digitally indicating the identification number (ID) of the microarray disk 10, sampling conditions, and the like are arranged on the inner or outer circumference of the microarray disk 10. In addition, the trigger point (i.e., the starting point of the rotation) is indicated on the microarray disk 10 for controlling the rotation of the microarray disk 10, the irradiation of the excitation light L, the timing of the detection of the fluorescence, and the like. Specifically, indication of the trigger point is realized by arrangement of a reflection marker which radially extends in the direction of a normal from the center of the microarray disk 10 across the grooves, and each of the plurality of spots are regularly arranged with respect to the normal. For example, the plurality of spots may be located at angular positions each of which differs from the angular position of the normal (i.e., the trigger point) by an integer multiple of 45 degrees. Therefore, it is possible to uniquely assign an address to each of the spots on the basis of the distance from the center of the microarray disk 10 to the spot and the angular position of the spot with respect to the normal. Although not shown, in order to recognize the angular position, an arrangement for detecting the trigger point is provided in the fluorescence detection system 1. The arrangement includes a first optical system for applying laser light to the surface 13 of the microarray disk 10 and a second optical system for receiving reflected laser light, and the first and second optical systems have a common optical axis. In this arrangement, the microarray disk 10 is rotated while the laser light is applied to the microarray disk 10 through the first optical system, and a photodiode receives the reflected laser light through the second optical system, and converts the reflected laser light into an electric signal (trigger timing signal). Then, the controller 50 controls the irradiation of the excitation light L, the timing of the detection of the fluorescence, and the like on the basis of the timing of the trigger timing signal.

For example, consider the case where the spots are regularly arrayed along each groove at intervals of 45 degrees with reference to the trigger line (the normal), and the microarray disk 10 is rotated at the rotation speed of 7,500 rpm. In this case, seven dot-shaped spots are arrayed per revolution (in each of the concentric grooves). Since the fluorescence F is detected after a delay of one millisecond after the irradiation with the excitation light L, and the angles of the first and second positions a and b differ by 45 degrees, the one-millisecond delayed fluorescence emitted from the first spot (adjacent to the trigger line) can be detected when 2 milliseconds elapses since the detection of the trigger line (trigger timing signal). Subsequently, the one-millisecond delayed fluorescence emitted from the second to seven spots can be detected in succession at time intervals of one millisecond. Thus, the one-millisecond delayed fluorescence emitted from the seven spots is obtained during each turn after detection of the trigger line. Further, it is possible to increase the signal-to-noise ratio by repeating the detection of the delayed fluorescence emitted from spots in each groove a plurality of times, and accumulating the detection signals obtained from each spot. When the detection of the delayed fluorescence emitted from spots in each groove is completed, the excitation-light irradiation unit 30 and the fluorescence-detection unit 40 are moved to the next groove, and detection of delayed fluorescence emitted from spots in the next groove is performed in a similar manner.

Second Embodiment

Figure 4:
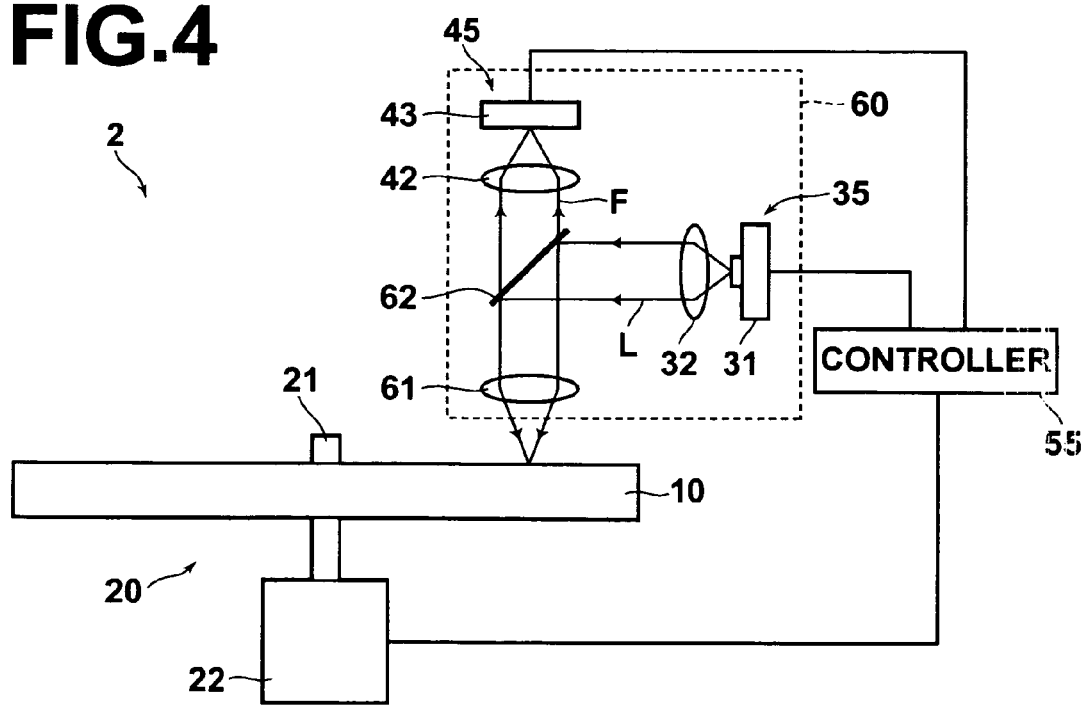
FIG. 4 is a diagram schematically illustrating a fluorescence detection system according to a second embodiment of the present invention, where a microarray disk is used.

FIG. 4 is a diagram schematically illustrating a fluorescence detection system according to the second embodiment of the present invention.

The fluorescence detection system 2 according to the second embodiment is different from the fluorescence detection system 1 according to the first embodiment in that an excitation-light irradiation unit 35 and a fluorescence-detection unit 45 are integrally formed in an optical unit 60.

The optical unit 60 comprises a condensing lens 61 and a half mirror 62. The condensing lens 61 is arranged above the specimen-fixed side of the microarray disk 10, makes the excitation light L converge on each biological specimen, and collects fluorescence F emitted from the biological specimen. The half mirror 62 is arranged above the condensing lens 61, passes the fluorescence F, and reflects the excitation light L.

The optical unit 60 operates as follows.

The excitation light L is emitted from the laser diode 31, collimated by the collimator lens 32, and reflected downward by the half mirror 62 so as to enter the condensing lens 61. Then, the excitation light L is focused by the condensing lens 61 so that each biological specimen is irradiated with the excitation light L. As a result of the irradiation, the biological specimen emits the fluorescence F. The fluorescence F is collected by the condensing lens 61, passes through the half mirror 62, and is then led to the optical detector 43 through the lens 42. Therefore, the position on the microarray disk 10 to which the excitation light L is applied coincides with the position on the microarray disk 10 from which fluorescence is detected. In addition, the optical unit 60 can be moved in the radial direction of the microarray disk 10 by a movement mechanism (not shown).

The controller 55 controls the rotation unit 20, the excitation-light irradiation unit 35, and the fluorescence-detection unit 45 so that the excitation-light irradiation unit 35 irradiates each of the biological specimens with the excitation light L while the rotation unit 20 rotates the microarray disk 10, and the fluorescence-detection unit 45 detects the fluorescence F emitted from the biological specimen when a predetermined time elapses since the biological specimen is irradiated.

Specifically, the controller 55 may control the rotation unit 20, the excitation-light irradiation unit 35, and the fluorescence-detection unit 45 so that the excitation-light irradiation unit 35 irradiates biological specimens in a portion of the spots (e.g., spots in a groove or in a set of two or more grooves) on the microarray disk 10 with the excitation light L while the rotation unit 20 gives the microarray disk 10 a predetermined number of turns. Then, the irradiation is stopped, and the rotation unit 20 again gives the microarray disk 10 the predetermined number of turns. While the irradiation is stopped, the fluorescence-detection unit 45 detects fluorescence F emitted from each of the biological specimens in the above portion of the spots at the time the biological specimen comes to the position from which the fluorescence-detection unit 45 can detect the fluorescence F (i.e., the position under the condensing lens 61). Thereafter, the above operations of irradiation with the excitation light L and detection of fluorescence are repeated for each of the remaining portions of the spots in a similar manner until all the biological specimens on the microarray disk 10 are irradiated and fluorescence from all the biological specimens is detected.

In the above operations of irradiation with the excitation light L and detection of fluorescence, the number of turns of the microarray disk 10 are predetermined on the basis of the rotation speed and the fluorescent lifetime of the labeling material. In addition, The timing of the detection of the fluorescence from each biological specimen is controlled on the basis of either the time necessary for a turn of the microarray disk 10 (which is determined on the basis of the rotation speed) or position information supplied from the rotary encoder.

Additional Matters

The fluorescence detection system according to the present invention is not limited to the first and second embodiments. All suitable modifications and equivalents which will readily occur to those skilled in the art are regarded as falling within the scope of the invention. For example, the fluorescence detection systems according to the first and second embodiments can be modified as follows.

(i) A lens array may be arranged above the microarray disk 10 for increasing light collection efficiency.

(ii) It is possible to use multiphoton absorption material for increasing the selectivity.

(iii) It is possible to use the servo technology for improving the tracking performance.

What is claimed is:

1. A fluorescence detection system comprising:
a substrate disk being rotatable and having a specimen-holding area on which one or more biological specimens are fixed, wherein the one or more biological specimens are fluorescence labeled;
a rotation unit which rotates the substrate disk;
an excitation-light irradiation unit which performs irradiation of each of said one or more biological specimens with excitation light;
a fluorescence-detection unit which detects fluorescence emitted from said each of the one or more biological specimens; and
a control unit which controls said rotation unit, said excitation-light irradiation unit, and said fluorescence-detection unit so that said each of the one or more biological specimens is irradiate with excitation light while the substrate disk is rotated by the rotation unit, and the fluorescence-detection unit detects said fluorescence emitted from said each of the one or more biological specimens when a predetermined time elapses since each of the one or more biological specimens is irradiated with the excitation light, wherein the substrate disk is arranged in such a manner that the center of the substrate disk is positioned at the center of rotation of the rotation unit, and wherein the excitation-light irradiation unit is arranged on the upper side of the substrate disk and irradiates a predetermined excitation-light irradiation position on the substrate disk with the excitation light from the upper side of the substrate disk, and wherein the fluorescence-detection unit is arranged on the upper side of the substrate disk and detects the fluorescence in such a manner that a fluorescence detection position on the substrate disk and the predetermined excitation-light irradiation position are at identical distances from the center of rotation of the rotation unit and at angular positions that are different by angle $\theta$ with respect to the direction of rotation of the rotation unit, wherein $\theta$ is not equal to 0;

and wherein the angle $\theta$ changes based on the speed of rotation of the substrate disk by the rotation unit.

2. A fluorescence detection system according to claim 1, wherein said one or more biological specimens are labeled with a fluorescent material having a fluorescent lifetime on the order of microseconds to milliseconds.

3. A fluorescence detection system according to claim 1, wherein said specimen-holding area is realized by one or more grooves spirally or concentrically arranged on the substrate disk.

4. A fluorescence detection system according to claim 3, wherein each of said one or more grooves has a width which is greater than a diameter of a light spot which said excitation light forms on said substrate disk.

5. A fluorescence detection system according to claim 1, wherein said substrate disk is opaque to said excitation light.

* * * * *